US006480280B1

(12) United States Patent
Hinata

(10) Patent No.: US 6,480,280 B1
(45) Date of Patent: Nov. 12, 2002

(54) DEVICE FOR DETECTING CRIZZLE IN THE MOUTH AND THREAD OF GLASS CONTAINERS

(75) Inventor: Kunio Hinata, Yokohama (JP)

(73) Assignee: Precision Co., Ltd., Yokohama (JP)

(*) Notice: Subject to any disclaimer, the term of this patent is extended or adjusted under 35 U.S.C. 154(b) by 0 days.

(21) Appl. No.: 09/529,003

(22) PCT Filed: Aug. 12, 1998

(86) PCT No.: PCT/JP98/03580

§ 371 (c)(1),
(2), (4) Date: Jun. 15, 2000

(87) PCT Pub. No.: WO99/18427

PCT Pub. Date: Apr. 15, 1999

(30) Foreign Application Priority Data

Oct. 6, 1997 (JP) ............................................. 9-289054

(51) Int. Cl.$^7$ ............................................... G01N 21/90
(52) U.S. Cl. ................. 356/428; 250/223 B; 356/240.1
(58) Field of Search ........................... 356/239.4, 239.5, 356/240.1, 428; 250/223 B

(56) References Cited

U.S. PATENT DOCUMENTS 5,496,996 A * 3/1996 Barnes et al. ........... 250/223 B
5,900,945 A * 5/1999 Hinata et al. ................ 356/428

* cited by examiner

Primary Examiner—Richard A. Rosenberger
(74) Attorney, Agent, or Firm—Armstrong, Westerman & Hattori, LLP

(57) ABSTRACT

A device for crizzle detection, provided with a means for rotating a glass container placed at an inspection position, a data collecting means which has N light projectors and M light receivers arranged on a generally semispherical mointing jig around the mouth or thread of the glass container and which is adapted to collect N×M pieces of data for each scan over the glass container, a means for rearranging the collected data, and a means for differentiating the rearranged data. At regular intervals or each time a predetermined number of glass containers have passed, data on acceptable containers for all or part of N×M channels are automatically collected to update the threshold values initially registered for acceptable containers based on the collected data. Thus, the rate of detection of crizzled glass containers in not lowered.

5 Claims, 7 Drawing Sheets

DEVICE FOR DETECTING CRIZZLE IN THE MOUTH AND THREAD OF GLASS CONTAINERS

TECHNICAL FIELD

This invention is directed to check detection device in the neck and finished portions of glass containers especially bottles, cups, etc. in a bottle manufacturing or filling line, and this invention more specifically concerns such a method which is suitable to the automation. Especially, this relates to the check detection device of the neck and finished portions of glass bottles with auto slicing function.

BACKGROUND OF THE INVENTION

Conventionally, in a bottle manufacturing and filling line, detection of checks in the neck and finished portions of a bottle was primarily carried out in the line by visual inspection, or by setting manually and visually emitters (a) and receivers (b) according to the types of bottles and to the types of check defects on public-known handling machines. The a:b by plural emitters (a) and receivers (b) occupy plural of inspection stations depending on the portion to be inspected.

Further another system which is to emit light by lighting system on the neck and finished portions of a bottle and to extract reflecting light as an electrical signal level by photoelectricity transformation element such as CCD camera, is proposed.

However, in the above conventional visual inspection, it is impossible to detect defects on high speed flowing line. In the inspection method of setting manually and visually plurals of emitters and receivers depending on the types of checks, it is impossible to detect where the defects exist and also, it is impossible to inspect all kinds of checks in neck and finished portions of a bottle. Further, in changing the mould of the bottle, it takes a long time to set emitters, etc.

Further, as the example using the latter inspection method of the above, the inspection system, which was disclosed in the journal of "Patent disclosure Showa 59-6524 Bi. 3", can be pointed out. In this journal, the system is composed of rotating bottles, emitting lights from one emitter on the neck and finished portions, and extracting continuously reflecting lights as a level information by electrical signal from the photoelectricity transformation element such as a CCP camera etc.

Further, as disclosed in the same journal, in this composition, deterioration of emitters due to time lapse, changing of brightness of the circumstance due to time lapse and variation of inspection sensibility of emitters due to change of voltage of the electrical source, will occur. Therefore, in order to protect the above variations, it is organized to control the amplification of process signals in order that the average figures of the process signal levels will come to the certain figures pre-set based on the average level of the process signals.

However, in this composition, it is impossible to elevate the inspection accuracy due to the fact that the standard levels of analog signal levels, which are gained by CCD cameras etc., are altered in response to the change by time lapse. Further, in this conventional inspection system, thought the detection of vertical checks in the neck and finished portions, for example, is comparatively effective, it still has the problem that the detection sensibility is low for the horizontal checks appeared along the screw of a bottle.

Accordingly, in this system, the inspection for all kinds of checks in the neck and finished portions for example are impossible and the problems of necessity of re-setting cameras, lights, sensibility etc. at the time of changing mould, are still there, same as the former visual inspection method.

Now, the inventor of this application developed a check detection device of neck and finished portions of a bottle having 640 multi-detection light channels of the emitters and receivers by setting for example 10 emitters (N=10) and 64 receivers (M=64) with dome shape against the bottle neck and finished portions for example (N×M=640 channels). This device is now applying the patent (1996 patent pending No. 255604).

According to the above method, detecting accuracy of defects is improved greatly compared with the conventional system because the data of 640 channels for example can be maintained per one inspection point i.e. one scan by the multi-directional emitting and receiving lights. Further, unexpected detects, which are in what part or to what direction of the neck and finished portions of bottles, the defects will occur, can be detected.

By the way, considering the condition of existing one emitter against M number of receivers for example, in the inspection system which the inventor of this application developed previously, the emitted lights to the neck and finished portions of the inspected bottles from the emitters are reflected and passed through at these portions and are in-put to each receiver of numbers of M which is arranged in each different position.

In this case, if the inspected bottles are good ones, the figures will be under the threshold figures of the differential level figures of the good bottles previously registered. An in case of the rejected bottles, if the angle position of an emitter and a receiver positioned 1:M is proper, in other words, if the defecting light can be received in this position, the differential level figures, which are output in either of receivers of M numbers, exceed the threshold figures and detect defects.

Similarly, in the inspection system having emitters of N numbers and receivers of M numbers which was developed previously by the inventor of this application, the probability of detecting defects by the multi-directional lights will become higher in proportion to the numbers of N and M.

Now, one problem in case of adopting the inspection system mentioned above is that generally a scores of molds for bottle building, exists in bottle manufacturing factories and especially molds of mouth type (angle type) among them are altered in every several days because of mold diminishing, improper building, etc. In other words, building molds are altered every day. At this time, small shape variation due to such a projection, a dent, etc., which is produced by the jointing of molds, will occur.

The second problem is that the position gap of the handling machine which is a rotating means for inspected bottles, will occasionally occur with time lapse due to its mechanical composition.

The third problem is that the phenomenon of eccentricity, position gap, etc. will occur at the time of bottle rotation by the handling machine because the specification of height, outside diameter, inclination, neck bending of bottles after the bottle building, are comparatively rough.

The above-mentioned three problems will actually be an important problem in this kind of inspection system. Especially, at the time of arranging N numbers of emitters and M numbers of receivers in each different position, the above-mentioned shape change, eccentricity, position gap of the inspected bottles will lead to the excluding good bottles, and to lower the yield rate of production greatly due to the multi-directional emitting and receiving lights.

In other words, the action of emitting lights from multi-direction to the neck and finished portions of bottles, and receiving lights multi-directionally, for example, is very effective at the point of elevating the detecting ability for the defects existence and for the defects portions as mentioned above. Further, the more the numbers of emitters and receivers are, the more the detecting ability of defects will be elevated. However, the problem of increase of the possibility of excluding good bottles due to the above three problems is still there.

SUMMARY OF THE DISCLOSURE

This invention aims to cope with the 3 peculiar problems mentioned above utilizing the characteristics of an inspection system, which has multi-directional light channels having N numbers of emitters and M numbers of receivers as mentioned above. Further, this invention aims to supply the check detection device of the neck and finished portions of glass bottles which can improve quality control by setting the mould change automatically depending on bottle types which was difficult previously, by overall detecting checks in the neck and finished portions of a glass bottle with no relation to the portion and type of defects, by detecting a bubble, a stone, a chipped and unfilled thread and deformation, and further by assorting defects into both portions and types.

Also, this invention aims to supply the check detection device of the neck and finished portions of glass bottles without lowering defects detection ratio by less adding registration of good bottles and doing automatic registration of good bottles at the initial registration.

In order to achieve the above objects, the present invention is directed to a check detector for the neck and finished portions of a bottle, which comprises:

a rotating means which is capable of rotating an inspection bottle on the inspection position;

a plurality of emitters and a plurality of receivers arranged on an approximately hemispherical fixture surrounding the neck and finished portions of an inspected bottle as a center;

means for obtaining N×M data per single scanning to the inspected portion of said inspected bottle mentioned above wherein N is a number of emitters and M is a number of receivers;

means for assorting the data obtained;

means for differentiating the data means for comparison process of threshold figures which is to judge whether the differential output from the above differential means will exceed the fixed threshold figures or not.

means for collecting automatically the data of a good bottle of all or partial channels of N×M in each periodic time or in each passing numbers of glass bottles against the threshold figures initially registered and decided as a good bottle; means for enforcing automatic setting process which is to reset new threshold figures by 1) which is produced by adding the certain amount of margin figures on the differential figures of the collected data as the threshold figures, 2) against threshold figures newly set, repeating continuously the action of collecting automatically the data of a good bottle of all or partial channels of N×M in each periodic time or in each passing number of glass bottles and adding in order the certain amount of margin figures on the differential figures;

In other words, in this detection device of neck and check portions of glass bottles, inspection bottles are rotated in check position, N numbers of emitters and M numbers of receiver are arranged on the approximately and preferably hemispherical fixture around the neck and finished portions as a center, and then N×M numbers of making bright processing is done by the receivers on each inspection point under the constant intervals on all circumference of the neck and finished portions of glass bottles.

The term of "making bright processing" means obtaining a receiving light. The term "inspected point" means an area where emitting and receiving lights are focused on an inspected bottle per one scan.

At this time, L×N×M numbers of light process data are collected assuming inspection scans of all circumference of the inspected bottle to be L.

Next, by known assorting method of data, which assort data from each emitter and receiver according to channel units, assorted data can be obtained. This is called data assorting process. Then, differential process of data from receiving light is done according to each N×M receiving light in the above L. This differential process means the generally known process of difference and is treated by known differential method. By this differentiating, a changing point of brightness and darkness and changing amount of receiving light are detected;

1) For a good bottle, the judge level of the differential level is automatically set according to N×M channels for such a level that any of the amount of change detected in the above does not exceed the threshold data, then a check is not detected.

2) For a defective bottle, a check is detected since some of the differential data of N×M channels exceed the judge level of the differential level, and then exclusion signal works and omit this.

The "judge level of the differential level" means a value, which is differentiated, and a predetermined value with a fixed margin.

In the present invitation, interference between a plurality of emitters and receivers does not occur, since emissions from each emitter are not simultaneous. Thus, detecting checks can be made exactly and with over-lapping.

Similarly, detection of a bubble, a stone, a chipped and unfilled thread and deformation which are known defects in the neck and finished portions of a bottle can be detected, since in the present invention, the reflected light can be detected and changing of the reflected light direction can also be detected. Further, particularly, with respect to finished top surface, of the neck and finished portions, a top surface line over finish, unfilled finish, over press finish and bubble on finish etc., can also be detected.

Further, the check detector of the present invitation is capable of assorting defects into both portions and types, and, therefore, users are capable of improving the quality control and are capable of raising the productivity. Namely, against the N×M channels, a user is able to set the type of defects and is then able to read the assorting in each counter.

Further, the initial registration of a good glass bottle is done by the registration of the base patterns of finish, thread, neck and shoulder portions of a glass bottle, and also done by the numbers of 6~24 which are almost equal to the registration numbers of star wheel sections. Then, on line inspection follows.

Further, known reflected lights on the inspection portion of the inspected items in each N×M channel of the good registration are collected around the bottle by the receivers, and new threshold values are set by adding allowance values which are voluntary setting values to the differential values of the above data. In this case, if the above differential values are detected in the range of allowance values, judgement of "Good" is given and if the above differential values are detected out of the allowance value, judgement of "No good" is given. This procedure is done on all channels of N×M and is done on all or part portions of finish, thread, neck and shoulder of a glass bottle and around the bottle, and then, judgment of "Good" or "No good" for the inspected item is done. In this case, among the above differentiation values if, among channel numbers, the numbers which exceed allowance value, exceed judgment values set up voluntarily, they are judged as "No good" and excluding signals are emitted. To the contrary, the above channels do not exceed judgement values, they are judged, as "Good" to emit excluding signal.

Now, the inspection process for a bottle represented by a glass bottle is completed and this inspection process is done continuously.

At this time, differential values of N×M channels which are judged "Good" are to be remembered, and then, differential values of N×M channels of good bottles against each inspection process numbers or each inspection process numbers with periodical intervals pre-set are to be remembered.

Then, according to each channel of N×M remembered, the above mentioned threshold value is calculated from either peak value, average value or standard deviation value of good bottles, and this threshold value is re-set. After that, the above treatment is done continuously.

A series of auto setting process of the above is called auto slice. And by this auto slice, variation of moulds, delicate shape change of moulding due to abrasion, variation of the system which holds and rotates bottles in each section of star wheels of handling machines, and variation with time lapse are automatically perceived and sensibility of the inspection can be automatically corrected or set.

Further, this sensibility of the inspection are corrected over all channels of N×M but according to the channels, the channels of which inspection sensibility becomes higher or becomes lower, will appear. However, this system will work in harmony with moulding condition and bottle handling condition, and then, proper inspection sensibility of each channel can be kept by lowering of the reject of good bottles.

According to this invention, check detection of neck and finished portions of a glass bottle can be done comprehensively, and troublesome setting of a mould change depending on bottle type can be conducted fast due to fixing of the emitters and receivers arrangement and to automatic setting of the sensibility. At the same time, defects such as a bubble, a stone, a chipped and unfilled thread, deformation etc. in the neck and finish portions of a bottle can be detected, and by assorting defects into both portions and type, quality control improvement can be achieved.

As for the emitters used in the present invention, LED emitters are preferably used because of high-speed emission. However, the type of emitters is not limited and laser beam may be used as the emitter.

As for the receivers used in the present invention, photo receivers are preferably used. However, the type of receiver, which can be used, is not limited and any conventional device for receiving and detecting light may be used so far as the variation of light amount from the emitters can be detected.

The emitters and receivers used in the present invitation can be either fixed or semi-fixed on a fixture, preferably positioned approximately hemispherically around an inspected bottle. The position of the emitters and receivers can be arranged most suitably from time to time against the inspected bottles.

In the present invention, the assorting of the defects to both positions and types can be achieved by the detection of the channel position.

By the inspection device in the present invention, which is constituted of the above, the accuracy of the inspection of the neck and finished portions of a bottle can be improved in the bottle manufacturing factories, and the time of the mould change according to the bottle kinds can greatly be shortened. Further, the analysis and counter measure for the defect causes are taken fast by properly expressing the information of the defect kinds. And then, the increase of the productivity and the promotion of the labor saving can be expected by the above. Furthermore, the shortening of the time of mould change and much saving of the labor of line operators at the on-line operation can be expected. The kinds of defects of the inspected portions can also be detected constantly due to the keeping of the inspection sensibility.

BEST MODE EMBODIMENT OF THE INVENTION

The following are the explanation of enforcement shapes of the check detection device of bottle neck and finished portions related to the present invention choosing glass bottles as the inspection item.

Figure 1:
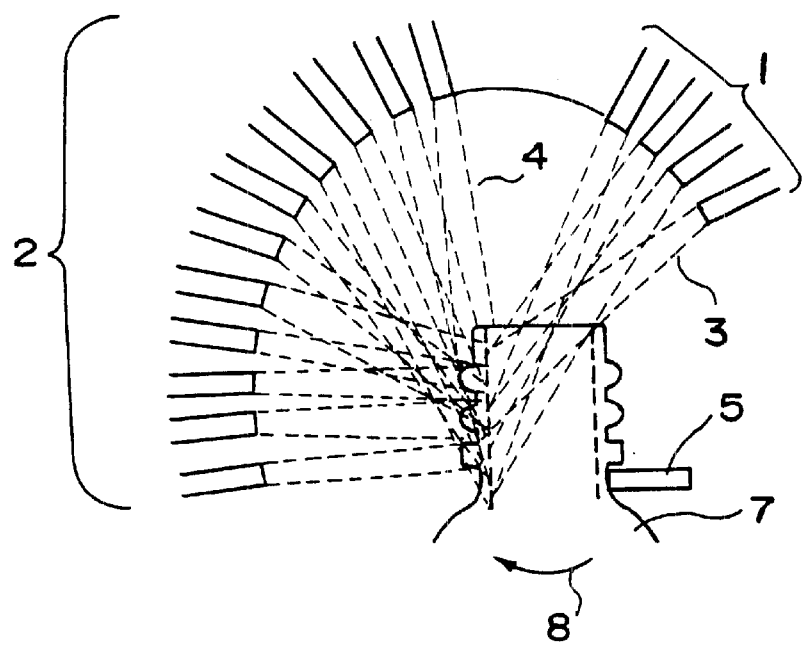
FIG. 1 is an illustration showing disposition of emitting sensor, receiving sensor, inspected bottles and area of emitter and receiver lights in an embodiment of the present invention.

FIG. 1 shows the position of each emitting sensor, receiving sensor and an inspected bottle. An inspection bottle 7 in the inspection position is rotated intermittently in the rotation direction shown at 8. A plurality of emitters is arranged in the emitter position 1 and a plurality of receivers is arranged in the receiver position 2. The emission and receiving of the light are conducted in the area of emitting lines 3 and receiving lines 4.

Figure 2:
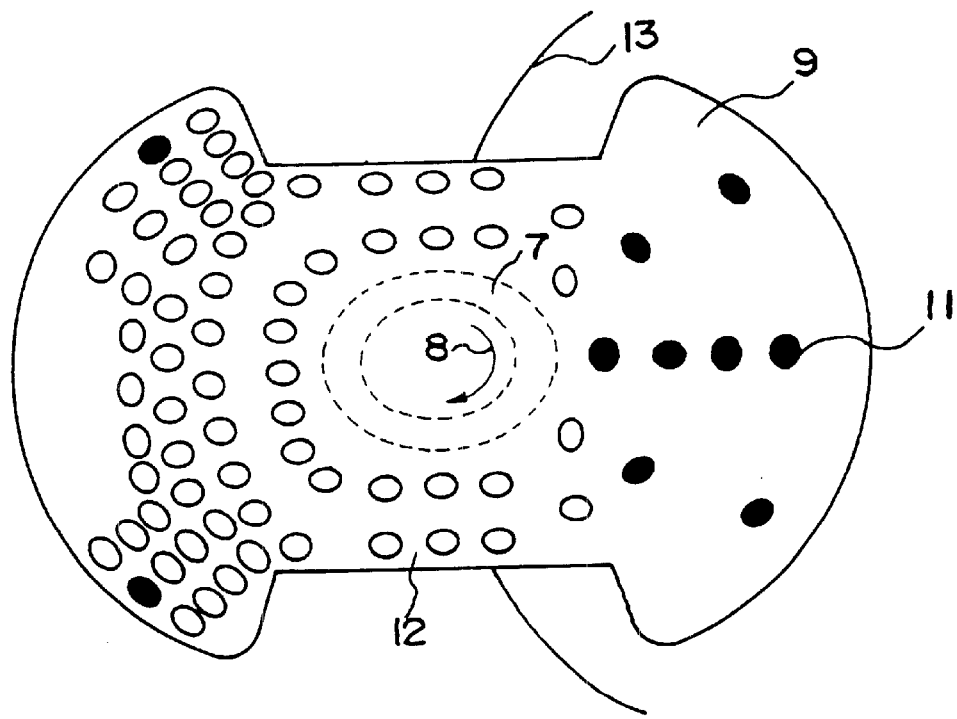
FIG. 2 is a detailed disposition of emitting sensor and receiving sensor on a fixture.

FIG. 2 shows the level position of each emitting sensor and receiving sensor on the inspection fixture. An inspection bottle 7 in the inspection position is positioned in star wheel 13 on the handling machine. Sensors of emitting light and receiving light are positioned on a fixture head 9 and ten emitters shown in 11, black mark and sixty four receivers shown in 12, white mark, are provided.

Figure 3:
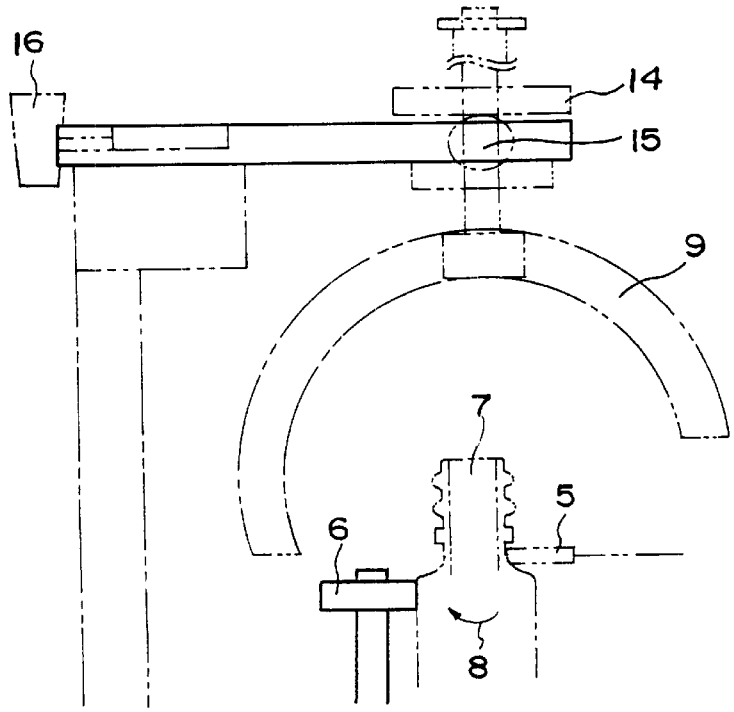
FIG. 3 is a side view illustrating dispositions of a fixture on a handling machine.

FIG. 3 shows the view of fixture head 9, on which emitting and receiving sensor are positioned as shown in FIGS. 1 and 2, being set on the handling machine. In this handling machine, a height adjuster 14, a right and left adjuster 15 and a front and rear adjuster 16 are provided. By operating knob 14 of the above height adjuster, the position of the fixture head 9, on which emitting and receiving sensors are arranged, can be adjusted up and down. By operating knob 15 of above right and left adjuster, the position of the above fixture head 9 can be adjusted right and left. Further, by operating knob 16 of the above front and rear adjuster, the position of the above fixture head 9 can be adjusted front and rear. Accordingly, the inspection position of the fixture head 9 can be adjustable according to the size of an inspected bottle 7. Further, as shown in FIG. 3, an inspected bottle 7 is rotated intermittently as shown in the arrow mark 8 by being held between the bottle rotating roller 6 which rotates on the body part of the inspected bottle 7 and the receiver roller 5 for the rotating bottle which contacts on the neck portion of the inspected bottle 7.

Figure 4:
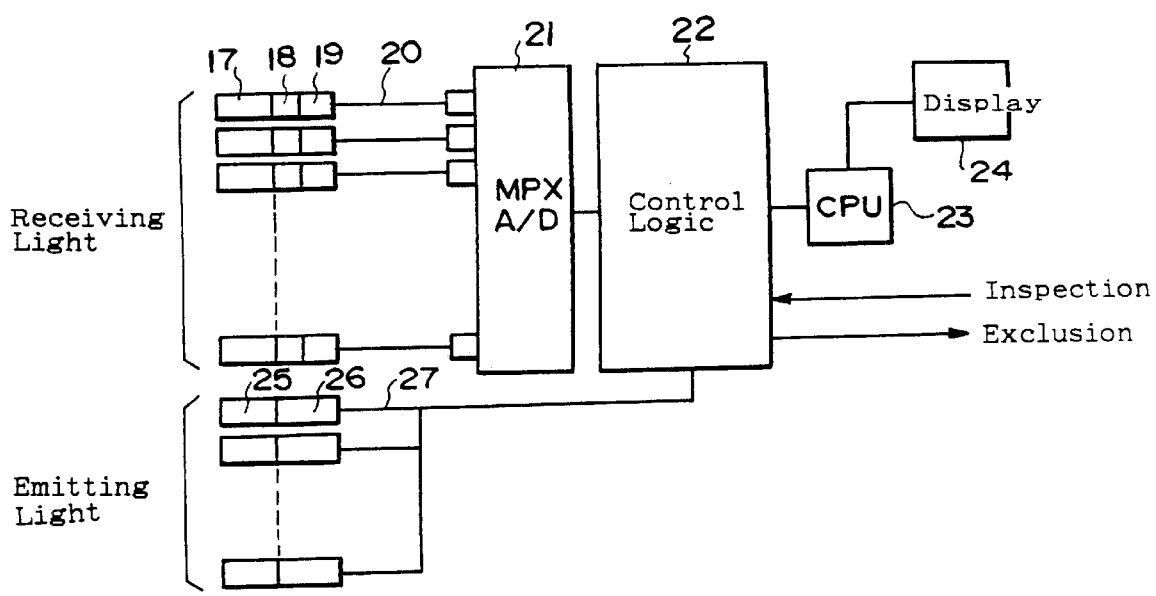
FIG. 4 is a block drawing illustrating the inspection device circuit of the present invention.

FIG. 4 shows a block chart of the circuit construction of the inspection device of the present invention. As shown in the figure, each emitter 11 of No. 1~No. 10 which is composed of an emitter element 26, an emitter lens 25 which gathers the light with beam shape from the emitter element 26 and an emitter cable 27 which supplies electrical signals to the above element 26 is connected to the circuit of control logic 22 by way of each cable 27.

Further, each receiver 12 of No. 1~No. 64 which is composed of a receiver lens 17, a receiver semiconductor 18 which converts the light received by the receiver lens 17 to the electrical signal, a receiver amplifier 19 which amplifies the electrical signal from the receiver semiconductor 18, and a cable 20 which transmits signals from the amplifier 19, is connected to the multiplex A/D converter circuit 21 by way of each cable 20.

Further, the above multiplex A/D converter circuit 21 is connected to the above circuit of the control logic 22 and is organized to sample the electrical signals (receiving light scan) from each receiver 12 by the order of the circuit of the control logic 22.

CPU 23 is connected to the above circuit of control logic 22, and then an indication part 24 is connected to this CPU 23. And the circuit of control logic 22 is organized to emit the excluding signals to the defect bottles with the timing of input of inspection signals.

Figure 5:
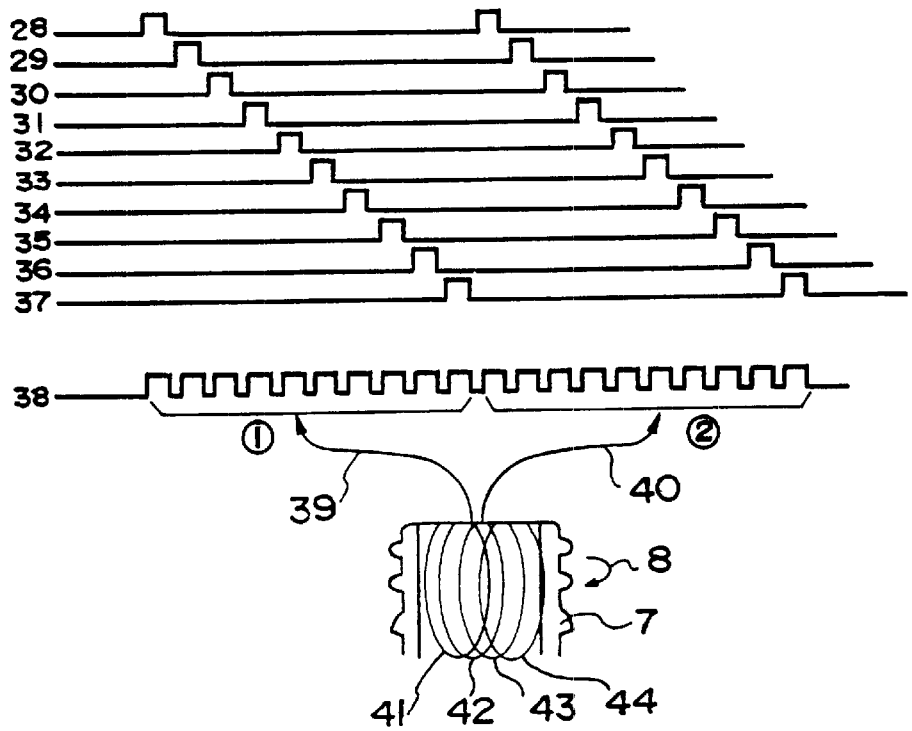
FIG. 5 is an illustration showing the relation between the timing sequence of emitter and receiver lights and an area of inspection of the inspection device shown FIG. 4.
Figure 6:
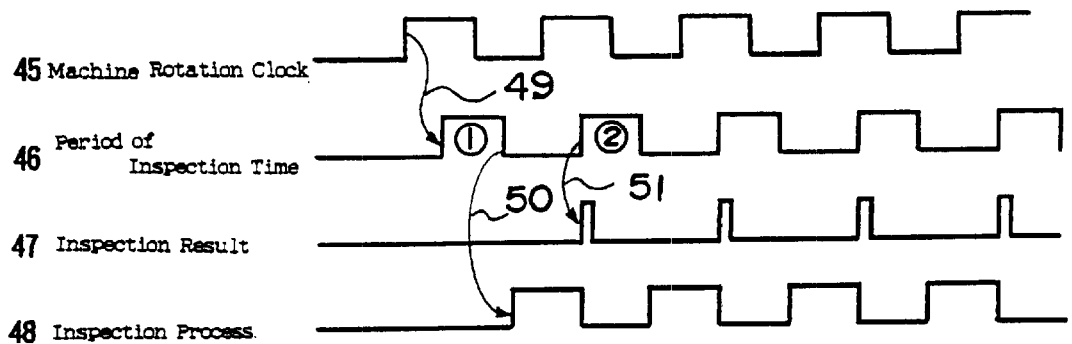
FIG. 6 is an illustration showing a timing sequence of an inspection process of the inspection device shown FIG. 4.

FIG. 5 and 6 shows the function of the circuit composition shown in FIG. 4. Each timing signal shown at 28~37 in FIG. 5 is produced from the circuit of the control logic 22 and emitting signals are given by turns with each time share against each emitter 11 of the above No. 1~No. 10. Further, the timing signal shown in 38 in FIG. 5 shows the sampling timing of receiving signals obtained from each receiver 12 of No. 1~No. 64.

In other words, the each timing signals shown at 28~37 is emitted from the circuit of the control logic 22, and with same timing, receiving signal from each receiver 12 is taken by controlling a multiplex A/D converter circuit 21 and with the timing shown at 38.

And, a multiplex A/D converter circuit 21 works for A/D conversion of receiving lights from each receiver 12, and for reading of receiving light data into CPU 23 through the above circuit of the control logic 22. In this case, with the timing shown at 38, receiving scan1 will be done in each one emission and this will be done for the all emissions from the emitter No. 1~No. 10 respectively. By this action, the gathering of data of one scanning by emitting and receiving light is finished. This one scanning is conducted fully around the bottle and gathering of the data is conducted.

Further, in the FIG. 5, 39 shows the receiving timing of the first scan and 40 shows the receiving timing of the second scan. In this case, 42 shows the inspection area of the first scan, 43 shows that of the second scan, 44 shows that of the third scan and 41 shows that of the Nth scan.

As mentioned above, as an inspection bottle 7 is rotated in the direction of 8, gathering of data is conducted fully around the bottle.

FIG. 6 explains the timing with the handling machine. If one period of the machine rotation clock 45 is assumed one handling of a bottle, the full data around an inspection bottle is gathered in the period of inspection time 46. The inspection processing 48 is conducted during the time prior to the next inspection time $\hat{2}$, and the inspection results 47 are output at the top of the inspection time $\hat{2}$. In this case, when the bottle is a defective bottle, an excluding signal is output from the above mentioned circuit of control logic 22.

In FIG. 6, 49 shows the bottle stop rotation timing. 50 shows the finish of bottle stop rotation timing. Further, 51 shows the timing of output of the inspection results.

Figure 7:
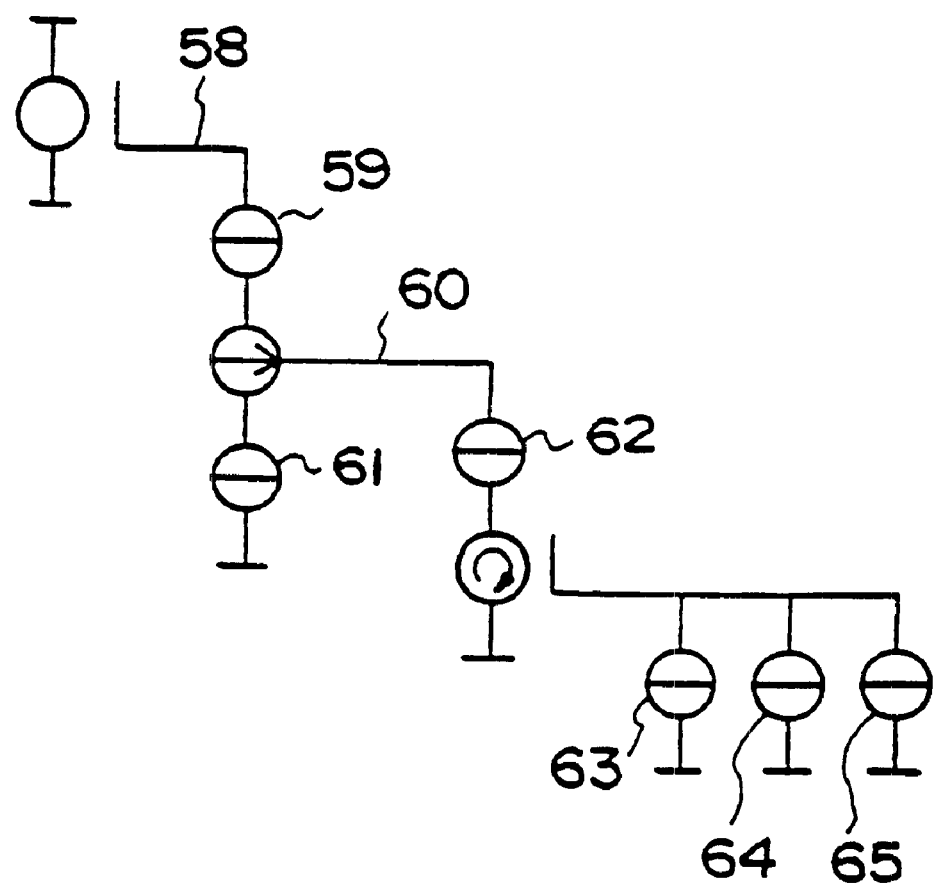
FIG. 7 is a sequence chart showing a sequence of procedure of the inspection device of the present invention.

FIG. 7 illustrates the outline of the treatment by soft ware in CPU 23. The preparation of the system motion is conducted by the operation of the initial setting process 59 by POWER ON 58.

Next, if the selection is Off Line 60, the preparation of Off Line process is conducted by the initial setting process of Off Line 62 and then, the selection of the process will follow. In the Off Line process, there are individual emitter screen process 63, defect detection monitoring process 64 and filing process 65, which are performed by the selection.

Figure 8:
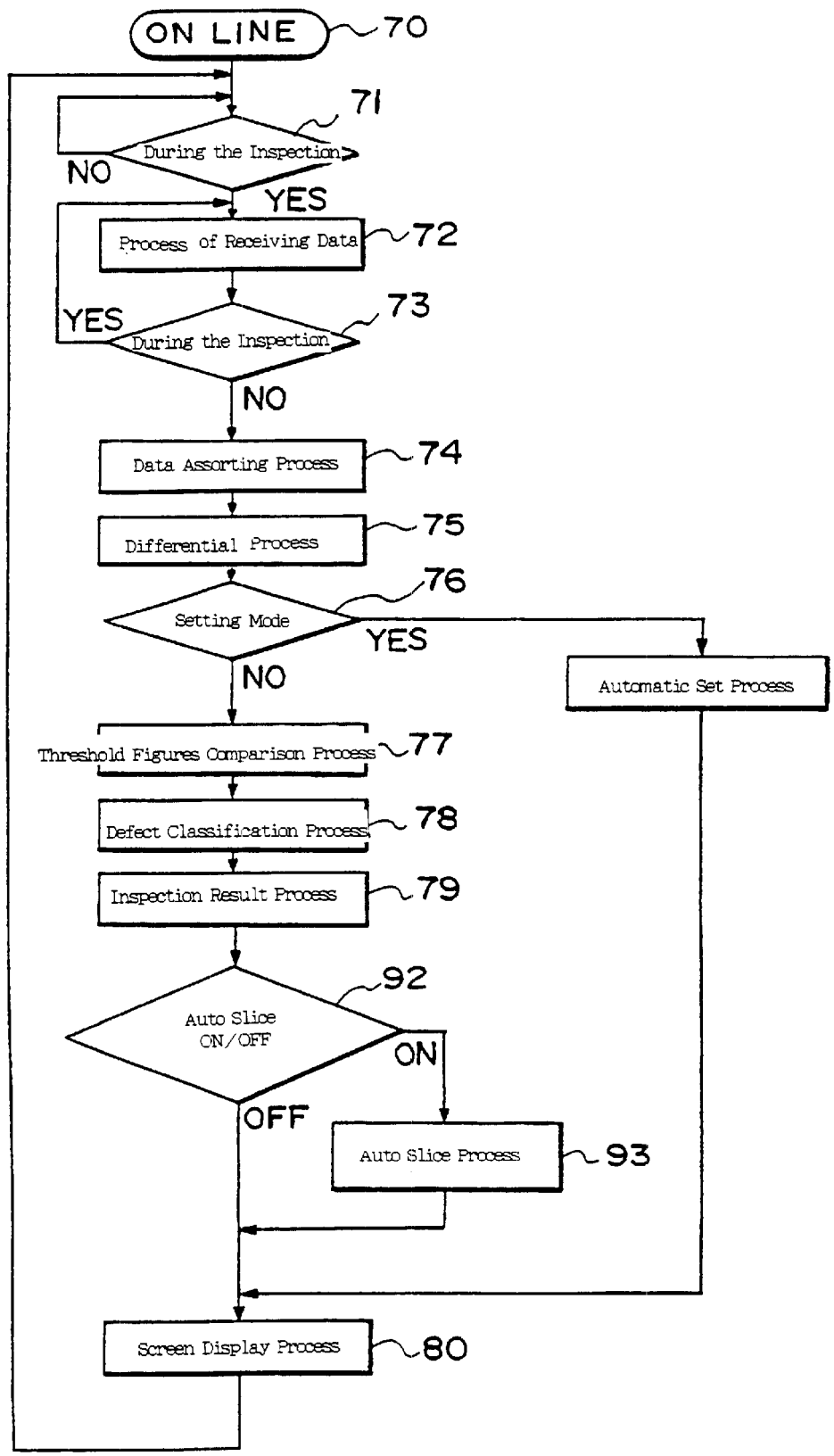
FIG. 8 is a flow chart showing operation process on line of the inspection device of the present invention.

If the selection is On Line, On Line process 61 is conducted. FIG. 8 shows a working flow chart of On Line process 61. The process is started by On Line start 70. Firstly, the judgment of being in inspection or not is done in the step 71. This is judged by comparing the signal of the "during the inspection" 46 in FIG. 6 by the signal comparison means.

In the signal comparison means, if the signal of "during the inspection" 46 is not detected (in case of No), it is waiting condition. On the contrary, if the above signal is detected (in case of Yes), the scanning of emission and receiving lights is started.

Then, in the step 72, CPU 23 performs the process of receiving data. In other words, CPU 23 reads 64 receiving data per one emitter and 10 emitting data per one scanning. These are equal to the amount for fully around the bottle, and the data for about 100 scans which correspond to the speed of the rotation of the bottle, will be read.

Next, it is judged whether it is still in condition of "during the inspection" or not in step 73. This will be done same as step 71 which is to perform the process of receiving data circulating to step 72 in case of the signal of "during the inspection" 46 being detected (in case of Yes).

And then, in case of the signal of "during the inspection" 46 being not detected (in case of No), the process of receiving data is stopped and data assorting process will be done by moving to step 74. In this step 74, the data of each emitter and each receiver are assorted to each channel as about 100 scans data, and the assorted data of about 100 scans of 10×64 channels are obtained.

In other words, as explained in FIG. 5, this assorting operation is to assort each data from receiving sensors gained with a time series, which is produced by giving emitting signals in turns to each emitter of No. 1~No. 10 with each timing of 28~37 and by collecting lights from the emitters in turn by each receiver of No. 1~No. 64 with each timing of 38.

In this case, each data is assorted in the order of the data gained from each receiver corresponding to each one emitter in every channel unit and these assorted data are differentiated as mentioned later. Accordingly, as these differential data can be extracted as the changing ratio to the next inspecting portion, the existence of defects such as checks can easily be detected.

Then, in step 75, the above assorted scan data are differentiated by the publicly known deferential process in each scan in order to calculate any changing amount of the received light data. For a good bottle, as the judge level of the differential level is automatically set for the N×M channels in such a level that any of the changing amount detected does not exceed the threshold value, a check is not detected. However, in the case of a check defect bottle, as any of the differential level data in the N×M channels exceed the judge level of the differential level, the bottle is detected as a check defect, excluding signal is emitted, and then, this inspected bottle is exhausted.

In step 76, setting mode is judge. Here, the judgment is done whether the process will be through automatic set process or not. In case of not automatic set process (in case of No), threshold comparison process is done by moving to step 77. If the data exceed the threshold value set by threshold comparison process, these are recognized as a defect of neck and finished portions of the bottles and the bottle are classified as the defect bottles in step 78. In this step 78, by means of defect classification process, the bottles are classified according to the defect classification, which is pre-determined based on the relation between the emitter and the receiver.

In step 79, process of the inspection result is done. Here, in case of defect bottles, a NG signal is output by an inspection result process and in case of good bottles, NG signal is not emitted.

Next, in step 92, the mode of auto-slice On/Off is judged. In case of judgment of auto-slice being On, auto-slice process later mentioned in step 93 is done and then screen display process mentioned in step 80 follows. In case of judgment of auto-slice being Off, screen display process mentioned in step 80 is done without auto-slice process.

In the mode of screen display process mentioned in step 80, inspection results are displayed as the mode mentioned later.

Figure 9:
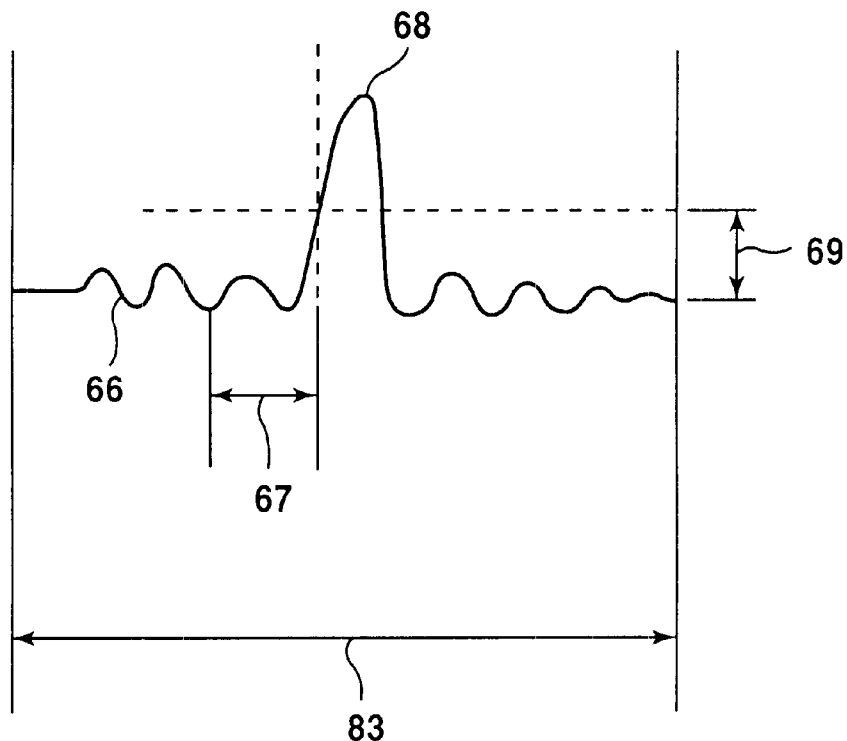
FIG. 9 is a drawing showing a differential process.

FIG. 9 illustrates differential process and threshold process. The scanning data 83 after assorting of data in about 100 scans from one emitter and one receiver among 10 emitters and 64 receivers mentioned above. In the example showed in FIG. 9, defect level data are shown in 68 and receiver sensor base data are shown in 66. If both data levels mentioned above are as shown in the figure, CP parameter 67 which is a differential comparison width is usually set from 1 to 10. The CP parameter is a parameter, which sets the choice of the data and difference of how many previous scanning. The slice parameter 69 which is set in the range from 5 to 100, is used as a threshold value. When the amount exceeds the threshold value, the bottle is determined to be a defect bottle.

Figure 10:
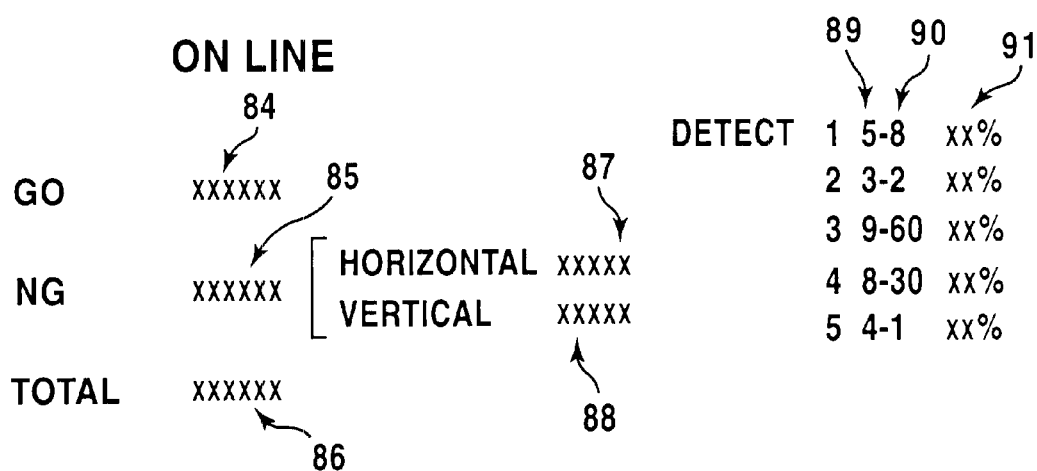
FIG. 10 shows an example of the screen at the time of operation process on-line.

FIG. 10 shows a screen 24 at the time of ON LINE. As illustrated in the Figure, the display areas of good bottles 84, defective bottles 85 and total number of inspected bottles 86 are monitored. As the inside figures of the number of defected bottles 85, the number of horizontal checks 87 and the number of vertical check 88 are also displayed. Further, the above inside figures of the defects detected are displayed for each emitter and receiver. In this display, the display areas of the emitters number 89, the receivers number 90 and the ratio of detection of defects 91 are set and these will be important data for investigating the reason for the defects, by gathering the data of defecting portions of the bottles as well as by feed back to the line.

Figure 11:
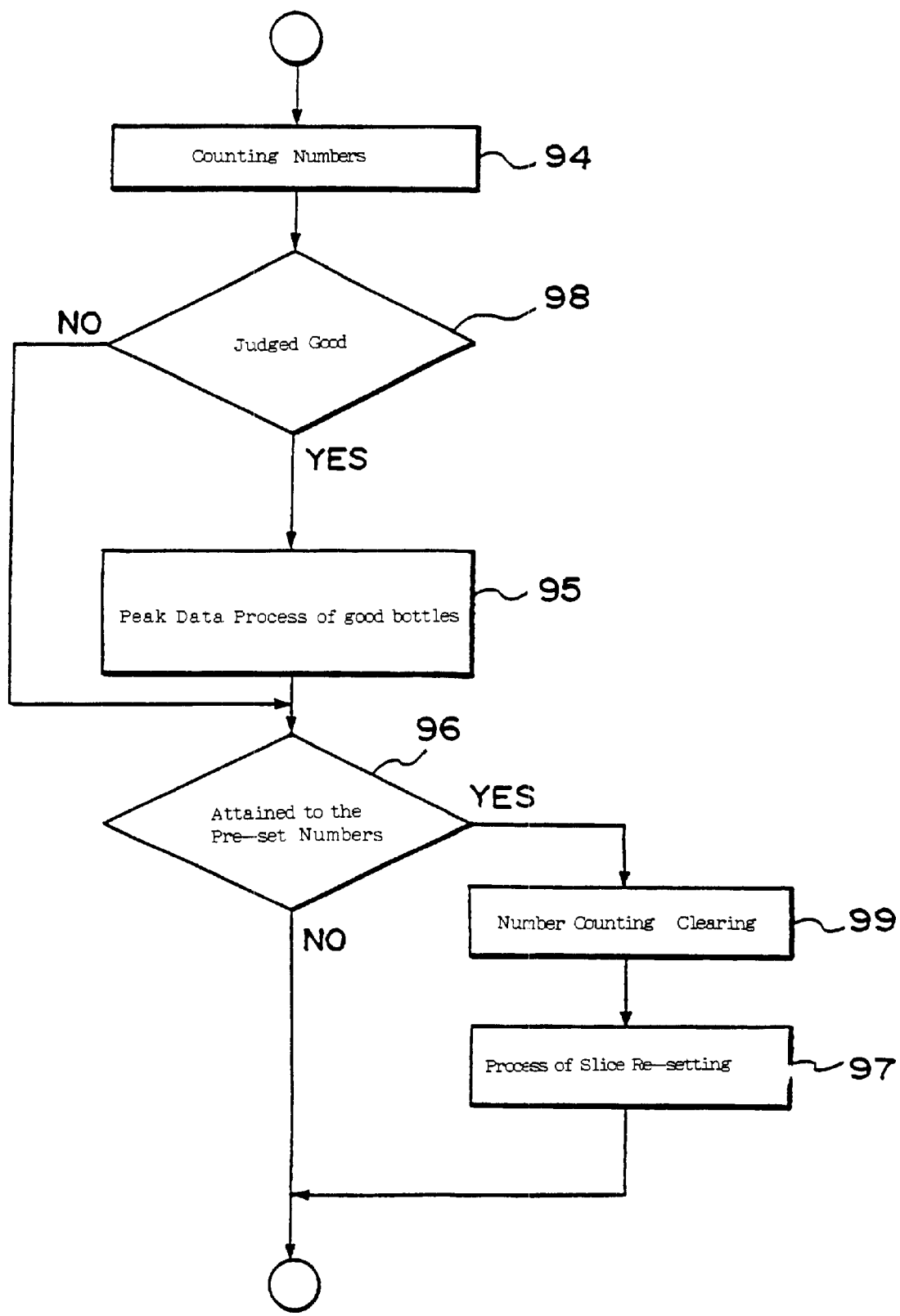
FIG. 11 is a flow chart showing operation of auto-slice.

In the FIG. 11, detailed process routine of auto-slice process, which is performed in step 93 of the FIG. 8, is shown. Namely in step 94 of the FIG. 11, the numbers of auto-slice are counted and in step 98, the data judged good (Yes) among the inspected bottles counted in the previous step, are picked up. Then, in step 95, peak data process of good bottles is performed based upon data picked up. In this peak data process of good bottles, differential level figures of all channels around the bottle neck and finished portions of the inspected bottles are remembered.

And, in step 96, it is judged whether the sum of inspected bottles of judged good (Yes) in the above step 98 and judged defect (No) in the above step 98, attained to the pre-set number or not.

In this step 96, peak data process of good bottles is continued in the above step 95, until coming to the pre-set numbers. At this time, the remembered differential level figures of all channels mentioned above are adopted from the peak data in each channel around the neck and finished portions of each bottle. And, in step 99, when it is judged that the pre-set numbers are attained in step 96, the figures of number counting in the number counter is cleared to zero.

Continuously, in step 97 which performs the process of slice re-setting, the slice figures which is the sum of the peak figure of differentiating level in each channel against all channels corresponding to around the neck and finished portions of good bottles set in step 96, and the margin figures pre-set are re-set in all channel and renewed. By this renewal of auto-slice, the increase of slice figures which is the direction to lower the slice sensibility is treated in the range of the above margin figures and in the case of the direction to elevate the slice sensibility, the sensibility is elevated automatically to the level of "Zero"+"Margin figure". In other words, the slice figure, which is one of threshold figures for judgment of "good or not", can automatically be adjusted against the irregularity of building mould of the bottle mouth, increase or decrease of differential level figures of good bottles mentioned above due to change with time lapse by abrasion etc., or increase or decrease of differential level figures mentioned above due to change with time lapse of handling by irregularity, variation, abrasion etc. in each section of the star wheel which keeps and rotates bottles on the handling machine.

Thus, by utilizing characteristics of the inspection system which has multi-directional emitting and receiving lights channels with N numbers of emitters and M numbers of receivers, an inspection system which can solve three peculiar problems mentioned above, can be provided and can elevate the reliability of the inspection system of this kind.

According to the examples of the actual operation, 0.2% of excluding ratio of good bottles and not less than 80% of defects detecting ratio for the inspection of mouth and shoulder portions of the bottle were attained, and serious defects could be detected nearly 100%.

What is claimed is:

1. A check detector in the neck and finished portion of a bottle, comprising:

a rotator for rotating an inspection bottle on the inspection position;

a plurality of emitters and a plurality of receivers arranged on an approximately hemispherical fixture arranged around the neck and finished portions of said inspection bottle as a center;

means for obtaining N×M data per single scanning against said inspection bottle, wherein N is a number of emitters, and M is a number of receivers;

means for assorting the N×M data obtained;

means for differentiating the assorted N×M data and creating differential output figures;

means for judging whether or not the differential output figures exceed threshold figures;

means for automatically collecting data of a good bottle of all or partial channels of N×M in each periodic time or in each passing number of glass bottles against the threshold figures initially registered and decided as a good bottle; and means for automatically executing steps of 1) renewing the threshold figures by setting new threshold figures which are produced by adding certain amount of margin figures on the differential figures of the collected data, 2) against the new threshold figures, continuously repeating an action of automatically collecting the data of the good bottle of all or partial channels of N×M in each periodic time or in each passing number of glass bottles and adding the certain amount of margin figures on the differential figures.

2. The check detector according to claim 1, further comprising means for renewing the threshold figures by considering the peak figure of a good bottle which does not exceed the threshold figures, average figures of good bottles' data collected, or the standard deviation figure.

3. The check detector according to claim 1 or claim 2, further comprising means for detecting all or part of unfilled finish, line over, over press, bubble, stone, check, chip unfilled thread, deformation and wrinkle which are kinds of defects in the neck, finished and shoulder portions of an inspected glass bottle.

4. The check detector according to claim 1 or claim 2, further comprising means for automatically adjusting or setting inspection sensibility by automatically reading variation depending on a forming die or variation depending on a forming batch.

5. The check detector according to claim 1 or claim 2, further comprising means for adjusting or setting inspection sensibility automatically by automatically reading variation depending on a system of holding or rotating a bottle in each section of the star wheel on the index type handling machine or the variation caused by time lapse.

* * * * *